US010065001B2

(12) United States Patent
Nessel et al.

(10) Patent No.: US 10,065,001 B2
(45) Date of Patent: Sep. 4, 2018

(54) APPARATUS WITH MOTOR WINDING RESISTANCE MEASUREMENT AND METHOD FOR CONTROLLING SUCH AN APPARATUS

(71) Applicant: Sanofi-Aventis Deutschland GMBH, Frankfurt am Main (DE)

(72) Inventors: Christian Nessel, Frankfurt am Main (DE); Barry Yates, Warwickshire (GB); David Moore, Leicester (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 169 days.

(21) Appl. No.: 15/031,663

(22) PCT Filed: Oct. 30, 2014

(86) PCT No.: PCT/EP2014/073280
§ 371 (c)(1),
(2) Date: Apr. 22, 2016

(87) PCT Pub. No.: WO2015/063193
PCT Pub. Date: May 7, 2015

(65) Prior Publication Data

US 2016/0263331 A1 Sep. 15, 2016

(30) Foreign Application Priority Data

Oct. 30, 2013 (EP) .................................... 13190924

(51) Int. Cl.
*A61M 5/20* (2006.01)
*A61M 5/315* (2006.01)
(Continued)

(52) U.S. Cl.
CPC .......... *A61M 5/31576* (2013.01); *A61M 5/20* (2013.01); *A61M 5/24* (2013.01);
(Continued)

(58) Field of Classification Search
CPC ............... H02P 8/12; A61M 5/20; A61M 5/24
(Continued)

(56) References Cited

U.S. PATENT DOCUMENTS 4,408,157 A * 10/1983 Beaubien ............... G01R 27/14
324/547
5,216,345 A 6/1993 Everly
(Continued)

FOREIGN PATENT DOCUMENTS

JP 08317684 A * 11/1996
JP 2009-278760 11/2009
(Continued)

OTHER PUBLICATIONS

International Preliminary Report on Patentability in International Application No. PCT/EP2014/073280, dated May 3, 2016, 6 pages.
(Continued)

*Primary Examiner* — Kawing Chan
(74) *Attorney, Agent, or Firm* — Fish & Richardson P.C.

(57) ABSTRACT

The invention relates to an apparatus, in particular for ejecting a fluid, having an electric motor (500), the motor comprising at least one motor winding (506*a-d*), having a control unit (656) for controlling the motor (500), wherein the apparatus further comprises an electronic detection circuitry (620) configured to determine an electrical quantity, the electrical quantity being a function of the electric resistance (Rw) of the motor winding (506*a-d*), and wherein the control unit (656) is configured to control the motor (500) as a function of the electrical quantity. The invention further relates to a method for controlling such an apparatus, comprising the steps of: determining an electrical quantity, the electrical quantity being a function of the electric resistance (Rw) of the motor winding (506*a-d*); and controlling the motor (500) as a function of the electrical quantity.

14 Claims, 12 Drawing Sheets

(51) Int. Cl.
*A61M 5/24* (2006.01)
*H02P 8/12* (2006.01)

(52) U.S. Cl.
CPC ...... *A61M 5/2448* (2013.01); *A61M 5/31546* (2013.01); *H02P 8/12* (2013.01); *A61M 2005/31588* (2013.01); *A61M 2205/33* (2013.01); *A61M 2205/3372* (2013.01); *A61M 2205/52* (2013.01)

(58) Field of Classification Search
USPC ..................................................... 318/568.16
See application file for complete search history.

(56) References Cited

U.S. PATENT DOCUMENTS

2002/0071225 A1 6/2002 Sheldon et al.
2008/0074075 A1* 3/2008 Davis .................. H02P 23/0077 318/800
2010/0002744 A1 1/2010 Sheahan
2010/0052586 A1* 3/2010 Krauth .................... H02P 6/182 318/400.32
2013/0234631 A1* 9/2013 Bateman ................. H02P 6/182 318/400.01
2013/0234640 A1* 9/2013 Bateman ................... H02P 6/26 318/400.35
2017/0184458 A1* 6/2017 Jefferies ................... G01K 7/16

FOREIGN PATENT DOCUMENTS

WO WO96/25965 8/1996
WO WO3/099357 12/2003

OTHER PUBLICATIONS

International Search Report and Written Opinion in International Application No. PCT/EP2014/073280, dated Jan. 23, 2015, 9 pages.
Rote Liste, “50. Hypophysen-, Hypothalamushormone, andere regulatorische Peptide u. ihre Hemmstoffe,” Chapter 50, ed. 2008, 20 pages.
European Communication in Application No. 14796452.2, dated Dec. 5, 2017, 4 pages.

* cited by examiner

APPARATUS WITH MOTOR WINDING RESISTANCE MEASUREMENT AND METHOD FOR CONTROLLING SUCH AN APPARATUS

CROSS-REFERENCE TO RELATED APPLICATIONS

This application is a U.S. national stage application under 35 U.S.C. § 371 of International Application No. PCT/EP2014/073280, filed Oct. 30, 2014, which claims priority to European Patent Application No. 13190924.4, filed on Oct. 30, 2013, the entire contents of which are incorporated herein by reference.

The invention relates to an apparatus, in particular for ejecting a fluid, having an electric motor, the motor comprising at least one motor winding, and having a control unit for controlling the motor. The invention further relates to a method for controlling such an apparatus. The apparatus may be a medical device, in particular a medicament injection device.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.
2. Attach a dose dispenser, such as a double-ended needle assembly, to a distal end of the dispense interface. In this manner, a proximal end of the needle assembly is in fluidic communication with both the primary compound and secondary compound.
3. Dial up/set a desired dose of the primary compound from the injection device, for example, via a graphical user interface (GUI).
4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.
5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.
6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

A device like the drug delivery device described above usually comprises at least one electric motor to provide the mechanical power for operation. For example the motor may move a drive train to exert a pressure on a bung of a cartridge within the device in order to eject a defined medicament bolus from the cartridge and out of the device.

The medicament amount ejected due to such a drive train movement usually directly relates to the movement of the motor. In order to improve the precision of the ejected medicament bolus the motor movement therefore has to be controlled precisely. In particular, attempts are generally made to adapt the motor torque to the force counteracting the motor movement, for example due to the resistance of the medicament when moving the bung of a cartridge. If the motor torque is too low, the motor may stall or move too little, so that the bolus ejected from the device is too small. If the motor torque is too high, the motor may move to fast, so that the bolus ejected from the device is too large.

Therefore there is a general desire to improve precision of the motor torque control for such devices. In the art this is usually done by empirically determining and then defining adequate motor parameters like the voltage and the current supplied to the motor windings so that the motor provides an adequate motor torque under normal conditions.

It was found however that temperature can have a significant impact on the operation of the device, so that even with the predefined motor parameters the motor may provide deviating motor torques which are not optimal.

In light of the aforementioned, certain aspects of the disclosure provide an apparatus with improved motor torque control even for different conditions of the apparatus with respect to temperature. Certain aspects of the disclosure provide a method for controlling such an apparatus.

Certain aspects of the disclosure can be implemented as an apparatus, in particular for ejecting a fluid, having an electric motor, the motor comprising at least one motor winding, and having a control unit for controlling the motor, wherein the apparatus further comprises an electronic detection circuitry configured to determine an electrical quantity, the electrical quantity being a function of the electric resistance of the motor winding, and wherein the control unit is configured to control the motor as a function of the electrical quantity.

Certain aspects of the disclosure can be implemented as a method for controlling such an apparatus comprising the steps of determining an electrical quantity, the electrical quantity being a function of the electric resistant of the motor winding, and controlling the motor as a function of the electrical quantity.

The apparatus may be a delivery device, especially a drug delivery device such as a medical device configured to eject a drug agent (e.g. a dose of a medicament) such as an infusion device or an injection device, for instance an insulin injection pen. Injection devices may be used either by medical personnel or by patients themselves. As an example, type-1 and type-2 diabetes may be treated with patients themselves by injection of insulin doses for example once or several times per day.

In particular, the apparatus may be a medical device configured to deliver (i.e. eject) at least two drug agents from separate cartridges situated in two separate retainers.

Alternatively, the apparatus may for instance be configured to deliver (i.e. eject) a two-component adhesive from separate cartridges comprising a first component of the two-component adhesive (i.e. a binder) and a second component of the two-component adhesive (i.e. a hardener) respectively.

The apparatus comprises an electric motor which may be an AC or a DC motor. The motor comprises at least one motor winding. Electric motors generally comprise a stator and a rotor wherein at least one motor winding is situated on the stator or on the rotor to generate an alternating magnetic field making the rotor rotate. For example, the electric motor may comprise a stator with a number of magnetic poles and a rotor with a number of magnetic poles, each pole being equipped with a motor winding to generate the respective magnetic field. Alternatively, the stator or the rotor may also comprise one or more permanent magnets to provide for the magnetic poles.

The apparatus comprises a control unit for controlling the motor. The control unit is preferably a micro-processor control unit comprising a micro-processor and a storage with commands to control the motor. The storage may be a volatile or non-volatile storage such as a RAM, ROM, hard disk, flash memory or the like.

The control unit is configured to control the motor. In particular, the apparatus may comprise a motor drive circuitry which is configured to supply power to the motor windings and which is preferably controlled by the control unit to control the motor movement. The control unit may then for example control the amplitude of the voltage and/or of the current supplied to the motor windings during operation. Moreover, the control unit may control reversing of the voltage supplied to at least one motor winding to switch the direction of the magnetic field so that the rotor rotates. The apparatus may also comprise a pulse width modulation (PWM) circuitry, which may be part of the motor drive circuitry, and the control unit may be configured to control by pulse width modulation the electric power supplied to the motor and therewith the motor torque.

The apparatus comprises an electronic detection circuitry configured to determine an electrical quantity. The electronic detection circuitry may comprise analogue electronic components such as resistors, coils, capacitors, transistors such as bipolar transistors or field effect transistors, operational amplifiers and the like, and/or digital electronic components such as integrated circuits and/or analogue digital converters and/or digital analogue converters.

The electronic detection circuitry is configured to determine an electrical quantity, the electrical quantity being a function of the electric resistance of the motor winding. The electrical quantity may for example be a voltage, a current, a resistance such as the electric resistance of the motor winding or the like. The electrical quantity may also be a digital signal, for example output by an analogue digital converter configured to convert an analogue signal (such as a voltage) to a digital signal. The electrical quantity may be a linear or nonlinear function of the electric resistance of the motor winding.

The control unit is configured to control the motor as a function of the electrical quantity. In particular the control unit may be configured to control the motor torque as a function of the electrical quantity. For example, the control unit may be configured to control the amplitude of the voltage and/or of the current supplied to one or more motor windings as a function of the electrical quantity.

It was found that temperature changes in the environment of the apparatus have a significant impact on the motor output which may lead to motor torques that are not optimal when controlling the motor with a predefined parameter set that is optimal under normal conditions, for example at room temperature. Such temperature changes may also be induced by the apparatus itself, for example of the at least one motor winding heats up during motor operation.

Temperature changes may for example have an impact on the lubricating effect of lubricants used within the apparatus in that for example at higher temperatures a better lubricating effect reduces friction within the motor and therefore increases the motor torque whereas at lower temperatures a reduced lubricating effect increases friction and therefore decreases the motor torque. Also the viscosity of a medicament to be ejected from the apparatus by means of the motor power may change with temperature so that for higher temperatures less torque may be needed than for lower temperatures. Moreover, the electric resistance of electrical components of the motor such as the electric resistance of the at least one motor winding or of electric components connected thereto is usually temperature dependent. For a motor with voltage supply of constant amplitude the current flowing through a motor winding depends on the inner electric resistance of the motor winding according to Ohm's law I=U/R with the voltage U, the resistance R and the current I. If at higher temperatures the inner electric resistance of the motor winding increases, less current will flow through the motor winding resulting in a weaker magnetic field and therewith in a lower motor torque.

With the apparatus described above it is possible to account for all these temperature-related effects as the control unit controls the motor as a function of an electrical quantity being a function of the electric resistance of the motor winding. As the electric resistance of the motor winding is a function of the temperature of the motor winding (which is assumed to be similar to the temperature of the apparatus), also the electrical quantity is a function of the temperature of the motor winding. A change of temperature will therefore result in a change of the electrical quantity so that the control unit may counteract temperature-related changes of the motor torque by controlling the motor accordingly as a function of the electrical quantity. In this way, the motor movement and in particular the motor torque may be precisely controlled even under different temperature conditions so that the operational precision of the apparatus such as the precision of a medicament volume ejected from the apparatus is improved.

The electrical quantity also provides a temperature indicator so that an additional temperature sensor which would complicate the apparatus construction and increase costs can be dispensed with.

The control unit may be configured to determine parameters for controlling the motor by means of a at least one defined function yielding at least one parameter for controlling the motor as a function of the electrical quantity. The function may be a linear or a non-linear function of the electrical quantity. Alternatively or in addition to that the control unit may also determine at least one parameter for controlling the motor from a look-up table which may for example be stored in a storage, the look-up table containing respective parameters for different values or ranges of values of the electrical quantity.

A number of embodiments of the apparatus and of the method for controlling such an apparatus will be described in the following. Some of the embodiments are described in particular with reference to the apparatus and some are described with reference to the method. However the embodiments of the apparatus also apply accordingly to the method for controlling such an apparatus and vice versa.

According to a first embodiment of the apparatus the electric motor is a DC motor, in particular a DC stepper motor, and the apparatus comprises a DC voltage source configured to supply a voltage to the motor winding.

The movement and motor torque of DC motors, in particular DC stepper motors, may be controlled very precisely so that such motors are often used for devices that require high motor precision such as medicament injection devices which rely on the motor precision to guarantee that a precise medicament dose may be ejected from the device. With the embodiment described above, motor movement and torque precision may be improved in particular if the apparatus is used under different temperature conditions.

According to a further embodiment of the apparatus the electrical quantity is a voltage. A voltage as electrical quantity allows a relatively simple configuration of the electronic detection circuitry since voltages may be easily tapped from a motor or a motor drive circuitry of the motor without disturbing the motor or requiring complicated modifications of the motor or the motor drive circuitry. In particular the electrical quantity may be a voltage which is a function of the voltage drop over the motor winding. The voltage drop over the motor winding directly depends on the motor winding resistance so that such an electrical quantity provides a measure for the motor winding resistance that is easy to evaluate.

According to a further embodiment of the apparatus the detection circuitry comprises a first sub-circuitry configured to provide a first voltage being a function of the voltage drop over the motor winding, and a second sub-circuitry configured to provide a second voltage being a function of the voltage of a voltage source, the voltage source being configured to supply a voltage to the motor winding, and wherein the electrical quantity is a function of the difference between the first and the second voltage.

The voltage drop over the motor winding is a function of the motor winding resistance, so that the first voltage being a function of the voltage drop is also a function of the electric resistance of the motor winding. Furthermore, the voltage drop and therewith the first voltage is also a function of the voltage of the voltage source. With the second voltage being a function of the voltage of the voltage source as well, a reference voltage is provided which may for example be configured such that the first and second voltage have the same value for a predefined condition, for example for a temperature of 20° C. The difference between the first and the second voltage then provides a direct measure for the deviation from the predefined condition which may be directly used by the control unit to control the motor. For example, the first and the second sub-circuitry may be configured such that the difference between the first and the second voltage is zero for a predefined temperature of for example 20° C., and is larger than zero for higher temperatures and smaller than zero for lower temperatures or vice versa. With an electrical quantity being this voltage difference of being a function thereof, the control unit may directly control the motor as a function of the deviation from normal temperature conditions.

According to another embodiment of the apparatus the detection circuitry comprises a differential amplifier having two input terminals and an output terminal, the first sub-circuitry comprises a first voltage divider connected in parallel to the motor winding, the central tap of the first voltage divider being connected to one of the input terminals of the differential amplifier, and the second sub-circuitry comprises a second voltage divider connected in parallel to the voltage source, the central tap of the second voltage divider being connected to the other of the input terminals of the differential amplifier. In this way it is possible to determine the electrical quantity as a function of the difference between the first and the second voltage by means of few and cheap electronic components that are easy to implement within the apparatus. The first and/or second voltage divider may for example comprise in each case at least two resistors connected in series with a central tap at the connection point of the two resistors.

According to a further embodiment of the apparatus the electronic detection circuitry comprises an analogue digital converter configured to convert the electrical quantity from an analogue signal to a digital signal, wherein the analogue digital converter has a discrete number range of possible outputs and wherein the analogue digital converter is configured such that a middle number of the number range is output for an analogue signal of the electrical quantity for a motor winding temperature between 10 and 40° C., preferably between 15 and 35° C. For example the analogue digital converter may be an 8-bit converter having a discrete number range of 256 discrete numbers from 0 to 255. The middle number of the discrete number range is the Nth number for a discrete number range of 2N numbers (even number of numbers) or of 2N+1 numbers (odd number of numbers). Accordingly, for the 8-bit converter the middle number is the $128^{th}$ number of the number range from 0 to 255, which is the number 127.

With the analogue digital converter being configured such that the middle number is output for an analogue signal of the electrical quantity for a motor winding temperature between 10 and 40° C., for example of 20° C., the digital signal may represent deviations from this temperature in both directions without digital clipping, i.e. without the analogue digital converter saturating. If for example the analogue digital converter converts the analogue output signal of the differential amplifier according to an embodiment described above, the analogue signal is zero for a defined temperature of for example 20° C. The analogue digital converter then may be configured such that a middle number is output for in input signal of zero. The temperature range from 10 to 40° C. is a typical temperature range for operation of such an apparatus under normal conditions.

The digital signal from the analogue digital converter, which itself constitutes an electrical quantity, can be directly used by a micro-processor control unit to control the motor, for example by calculating or determining from a look-up table motor parameters as a function of the digital signal.

The analogue digital converter may furthermore be configured such that the lowest number of the discrete number range is output for an analogue signal for a motor winding temperature between −20° C. and 10° C. and that the highest number of the discrete number range is output for an analogue signal for a motor winding temperature between 40° C. and 75° C. or vice versa. In this way the discrete number range may be completely covered for possible operation temperatures of such an apparatus, so that the temperature resolution of the digital signal from the analogue digital converter is improved.

According to a further embodiment the apparatus comprises a pulse width modulation (PWM) circuitry configured to control the motor torque by pulse width modulation, and the control unit is configured to control the PWM duty cycle as a function of the electrical quantity.

For a pulse width modulation control of the motor, a basically constant voltage supply to the motor winding is alternately switched on and off with a frequency that is much higher than the frequency with which the voltage supplied to a motor winding is reversed for reversing the magnetic field depending on the rotor position. The relation between the time periods during which the voltage is switched on ($T_{on}$) and the time periods during which the voltage is switched off ($T_{off}$) defines the PWM duty cycle. For example for a PWM duty cycle of 50%, $T_{on}$ equals $T_{off}$. For a PWM duty cycle of 75%, $T_{on}$ is thrice $T_{off}$. The higher is the PWM duty cycle, the higher is the average voltage and therewith the average power supplied to the motor winding. The motor torque may thus be effectively controlled by PWM.

By controlling the PWM duty cycle as a function of the electrical quantity, the control unit may counteract temperature effects on the motor torque and therewith keep the motor torque at the desired level with high precision.

Alternatively, if the motor torque is controlled by the amplitude of the voltage and/or of the current supplied to the motor winding, the control unit may also be configured to control the amplitude of the voltage and/or of the current supplied to the motor winding as a function of the electrical quantity.

According to a further embodiment of the apparatus the control unit is configured to estimate the temperature of the at least one motor winding as a function of the electrical quantity. For some applications it may be necessary to explicitly estimate the temperature of the motor winding or of the apparatus, which is assumed to have a similar temperature as the motor winding. For example, the temperature may be presented to the user for information or a warning may be output to the user if the temperature is outside a safe temperature range for operating the apparatus. With this embodiment, the temperature may be directly estimated from the electrical quantity without the need of an additional temperature sensor which otherwise would increase the complexity and production costs of the apparatus.

According to a further embodiment of the apparatus the control unit is configured to control the electric detection circuitry to determine the electrical quantity when the motor is at rest. In this way, detection of the electrical quantity is not disturbed by the motor movement. In particular, detection of the electrical quantity may require the at least one motor winding to be connected to a voltage source in a certain way which may not be possible during motor operation.

For example the motor winding may be connected to a positive and a negative voltage terminal of a voltage source by means of an H-bridge, the H-bridge comprising an upper and lower left switch to connect one terminal of the motor winding to the positive and negative terminal, respectively, and an upper and lower right switch to connect the other terminal of the motor winding to the positive and negative terminal, respectively. By closing the upper left and lower right switch the motor winding may be connected to the voltage source in a first direction and by instead closing the upper right and lower left switch the motor winding may be connected to the voltage source in an opposite second direction. The switches may for example comprise bipolar and/or field effect transistors and may be controlled by the control unit.

If the motor comprises more than one motor winding, for example four motor windings, each of the motor winding may be connected to the same positive and negative voltage terminal of the voltage source by means of a respective H-bridge.

In order to determine an electrical quantity being a function of the electric resistance of one motor winding, the switches of the H-bridges are preferably controlled in such a way that the respective motor winding is connected to the positive and negative terminal in a predetermined direction and that other motor windings are disconnected from the positive and/or the negative terminal. Such a switch configuration is difficult or even impossible during motor operation so that the electrical quantity is preferably determined when the motor is at rest.

Furthermore, interferences of the electronic detection circuitry due to voltages occurring during motor operation may be prevented when determining the electrical quantity when the motor is at rest.

According to a further embodiment the apparatus is a medical devise, in particular a medicament injection device. Medical devices such as medicament injection devices often rely on a precise control of the motor, in particular of the motor torque, since for example the precision with which a medicament volume is ejected from the device directly depends on the precision of the motor movement. Therefore, the apparatus described above is particularly advantageous for medical devices.

According to a further embodiment the apparatus is hand-held. Hand-held apparatuses are often apparatuses that are operated by laymen such as patients instead of particularly skilled personnel. A layman is however often not able to notice, yet to correct incorrect operation of the apparatus. Moreover laymen may disregard the possible impact of different temperatures on the apparatus. Therefore, an improved motor torque control in particular for different environmental temperatures is particularly advantageous for a hand-held apparatus.

These as well as other advantages of various aspects of the present invention will become apparent to those of ordinary skill in the art by reading the following detailed description, with appropriate reference to the accompanying drawings, in which.

Figure 1:
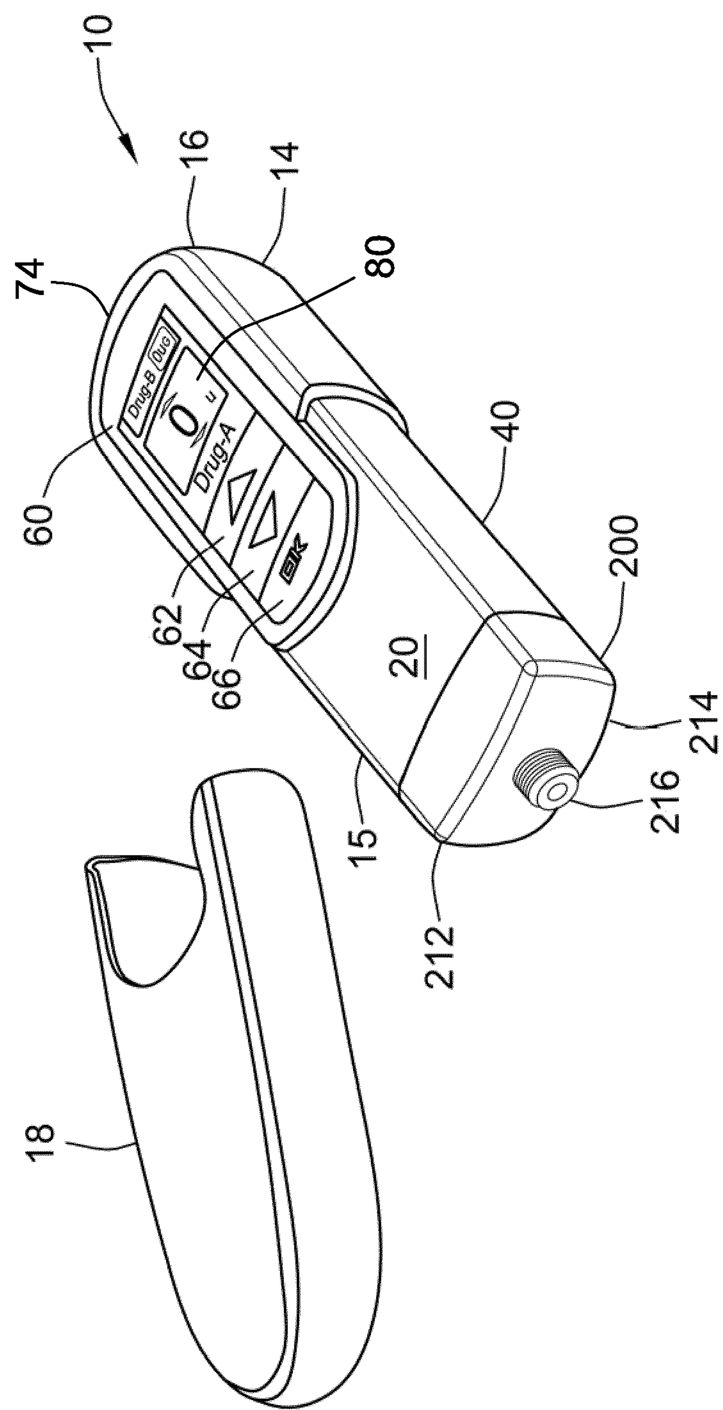
FIG. 1 illustrates a perspective view of a delivery device with an end cap of the device removed.
Figure 2:
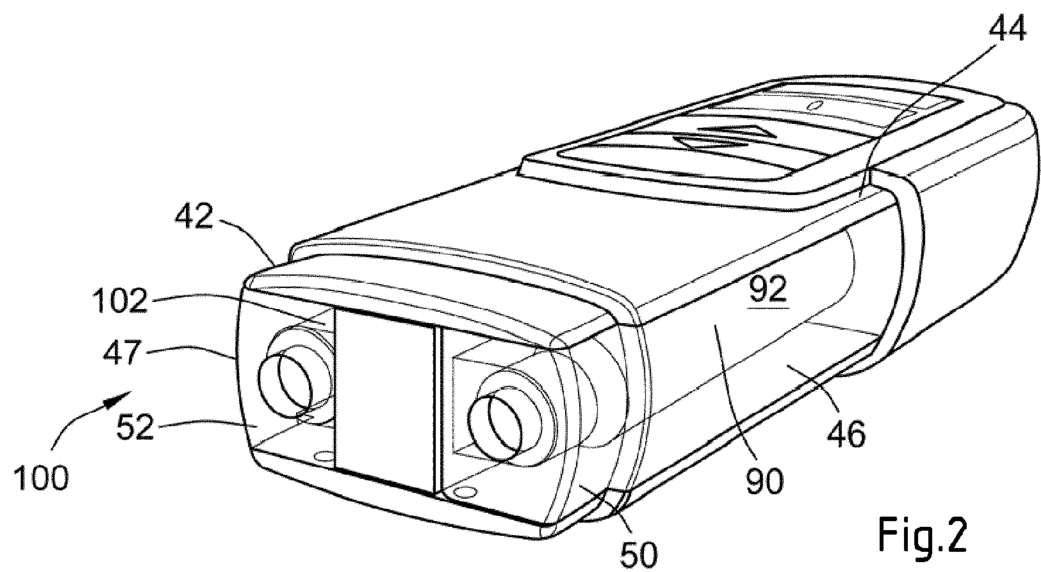
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
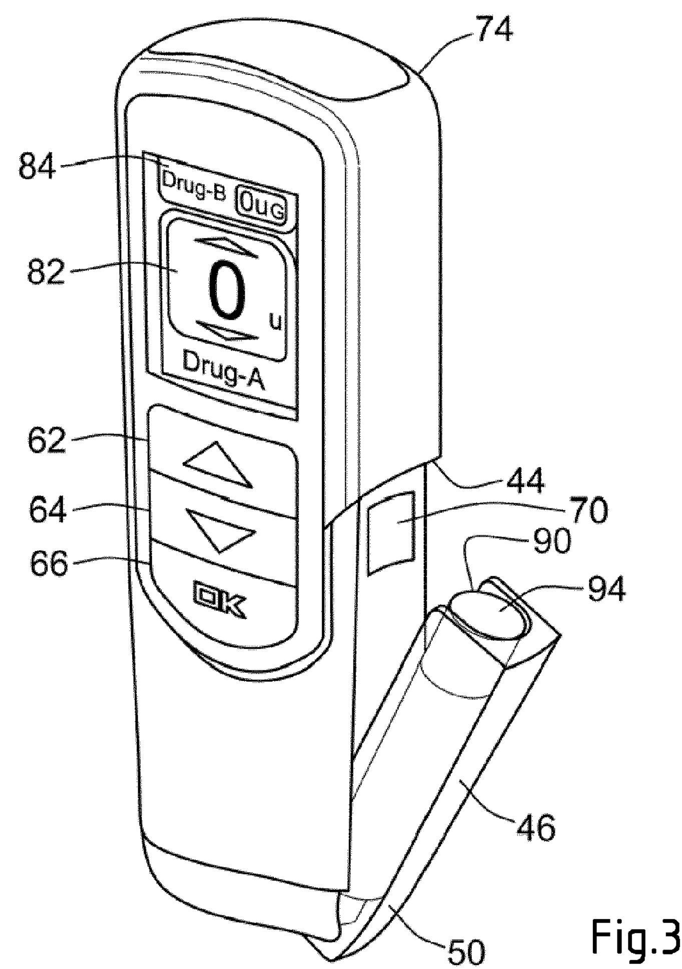
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
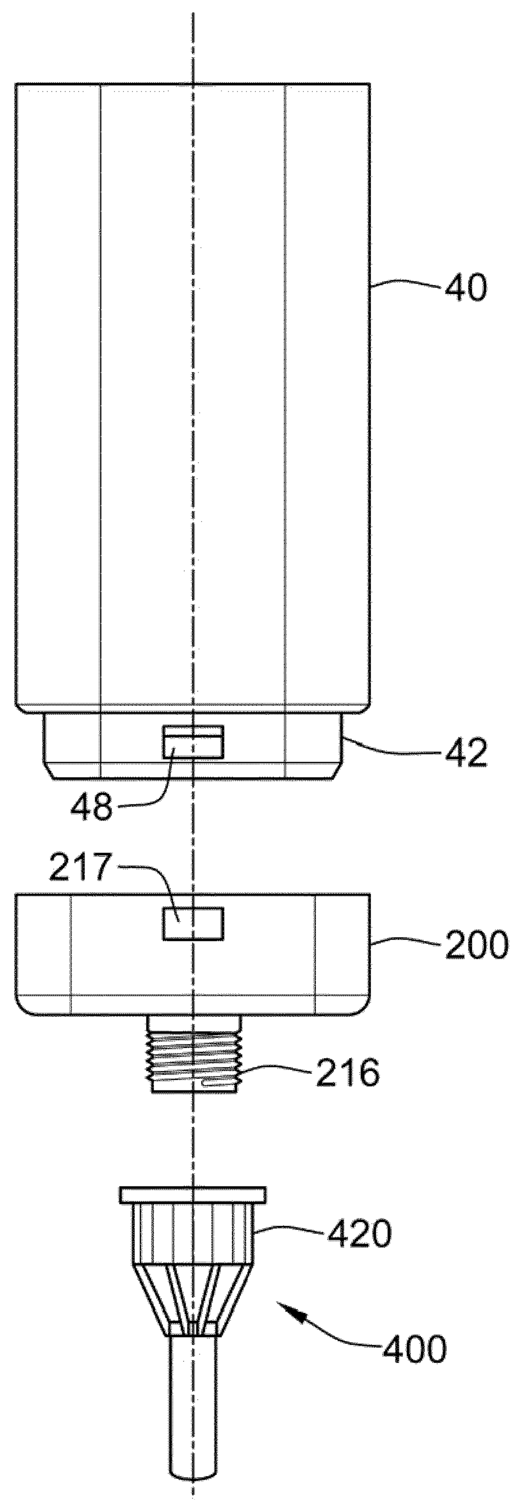
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
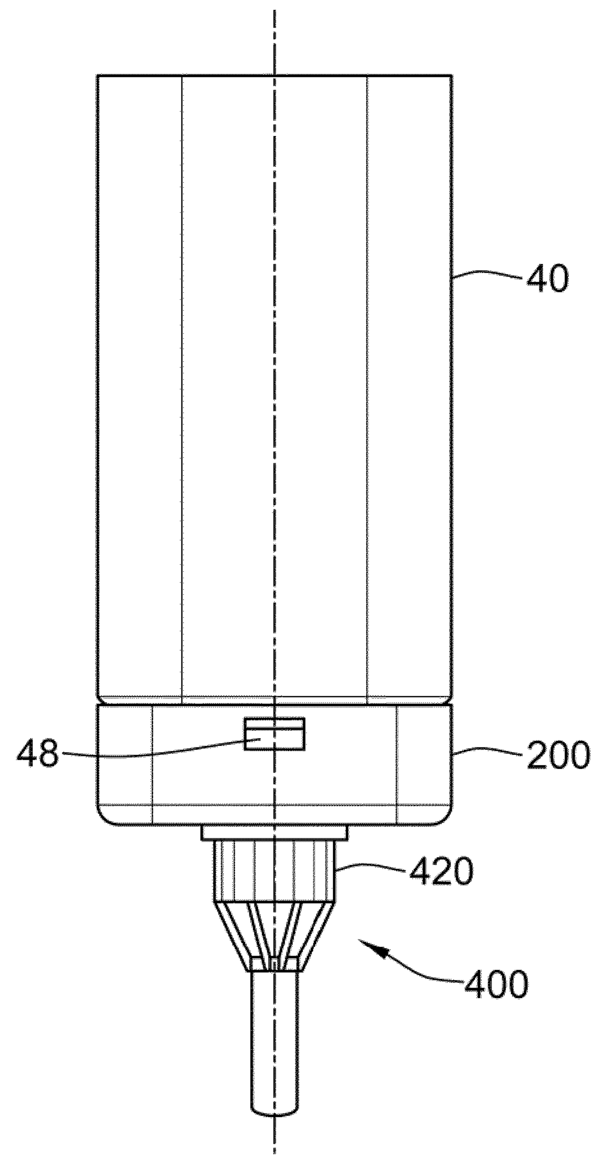
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means 48 between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
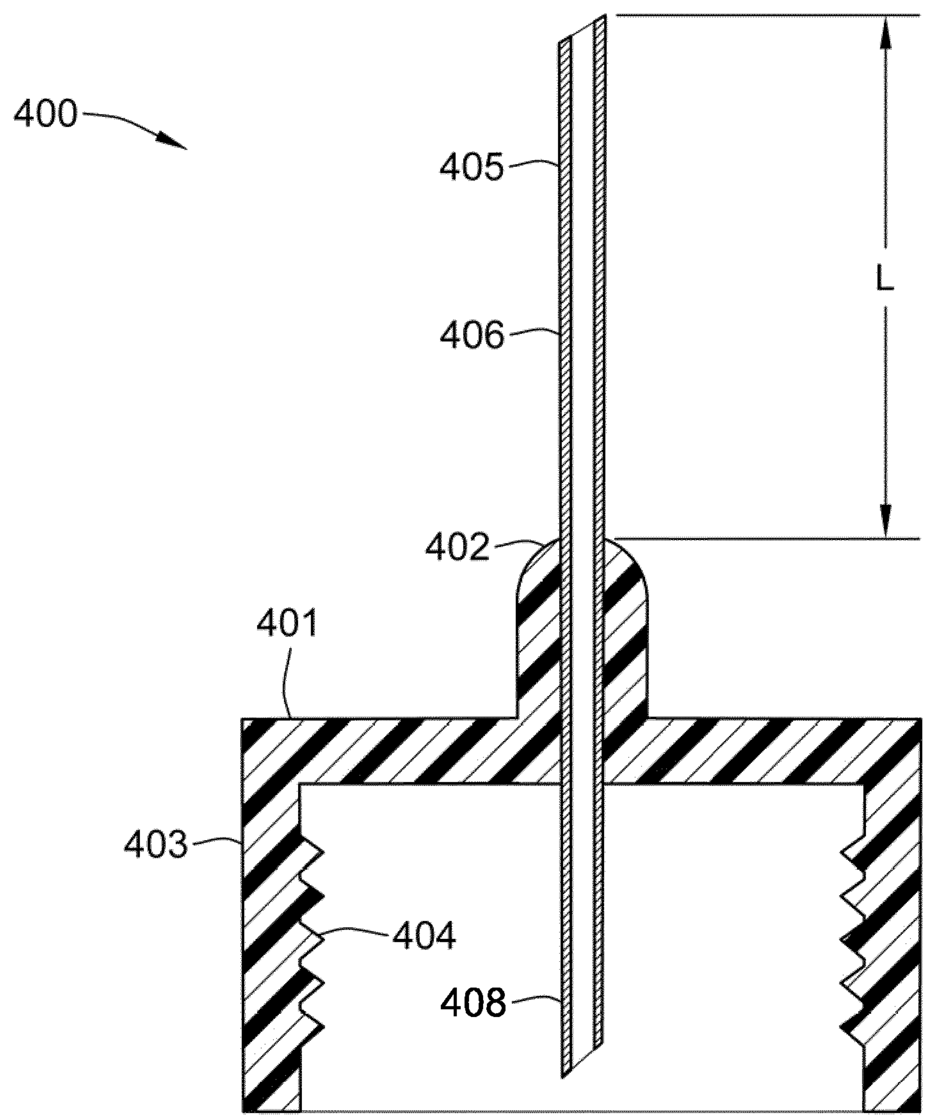
FIG. 6 illustrates one arrangement of a needle assembly that may be mounted on a distal end of the delivery device.
Figure 7:
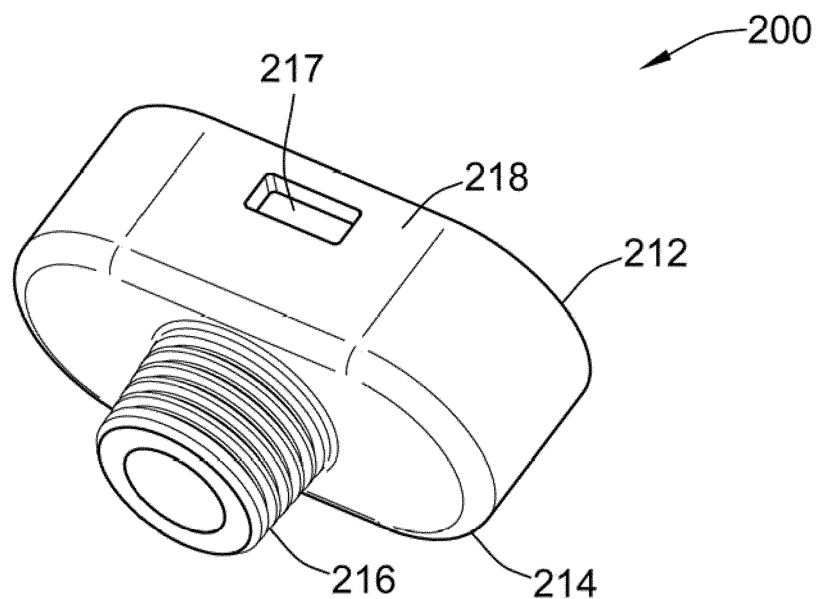
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

Figure 8:
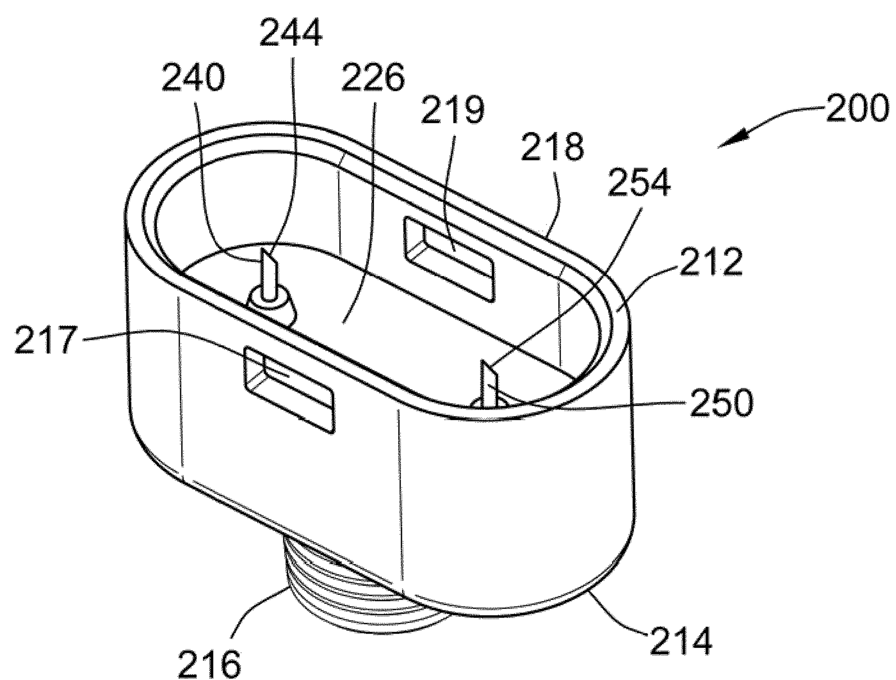
FIG. 8 illustrates another perspective view of the dispense interface illustrated in FIG. 4.
Figure 9:
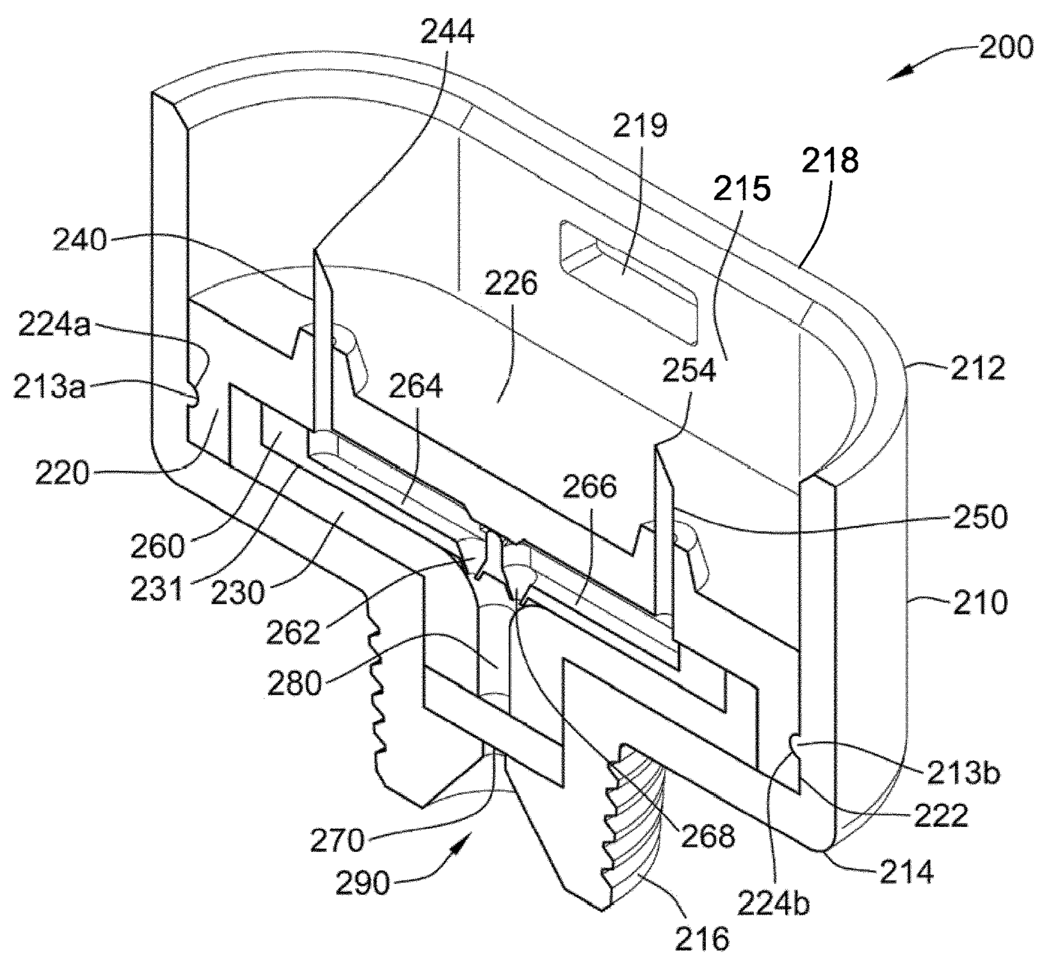
FIG. 9 illustrates a cross-sectional view of the dispense interface illustrated in FIG. 4.
Figure 10:
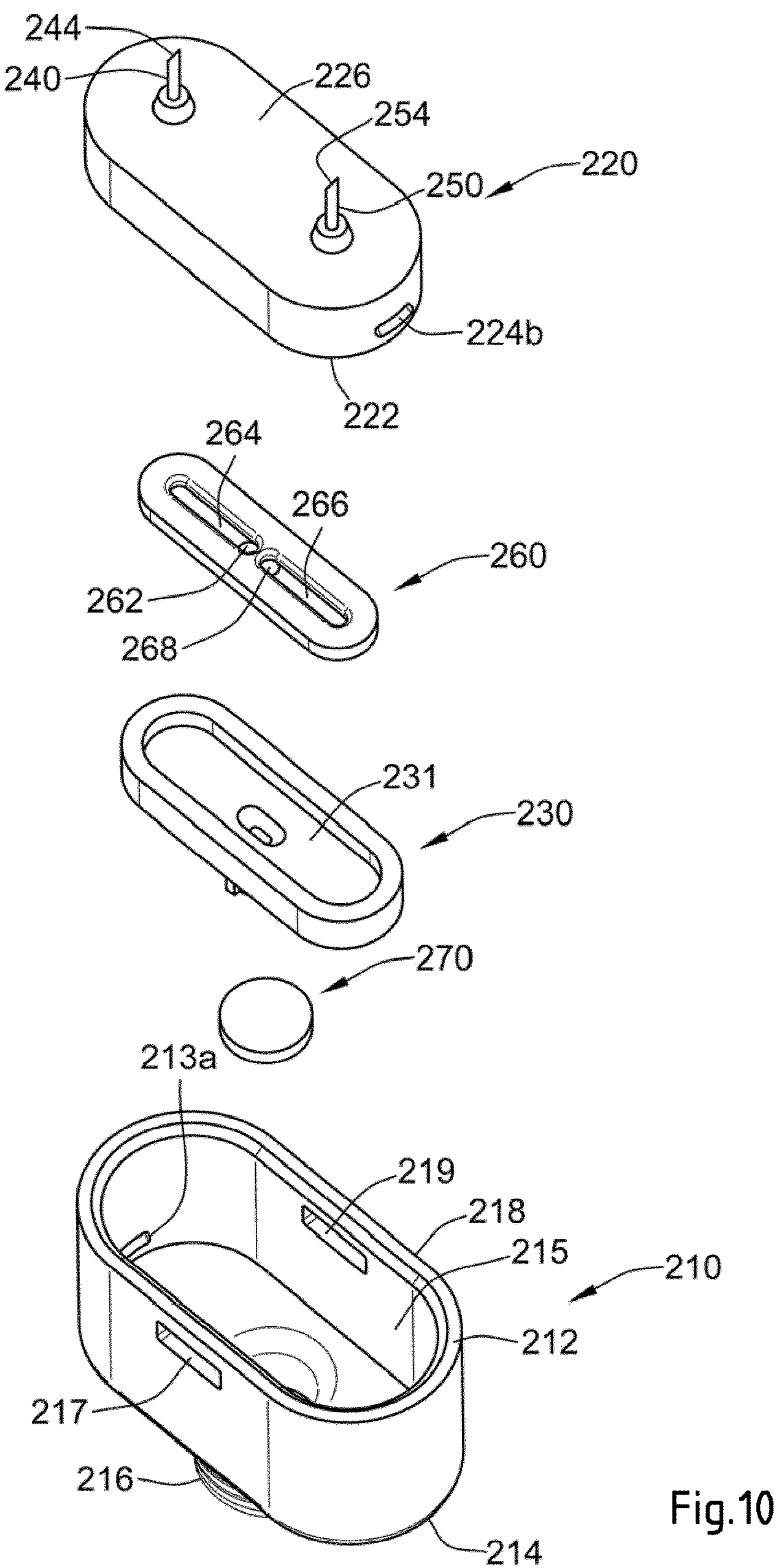
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
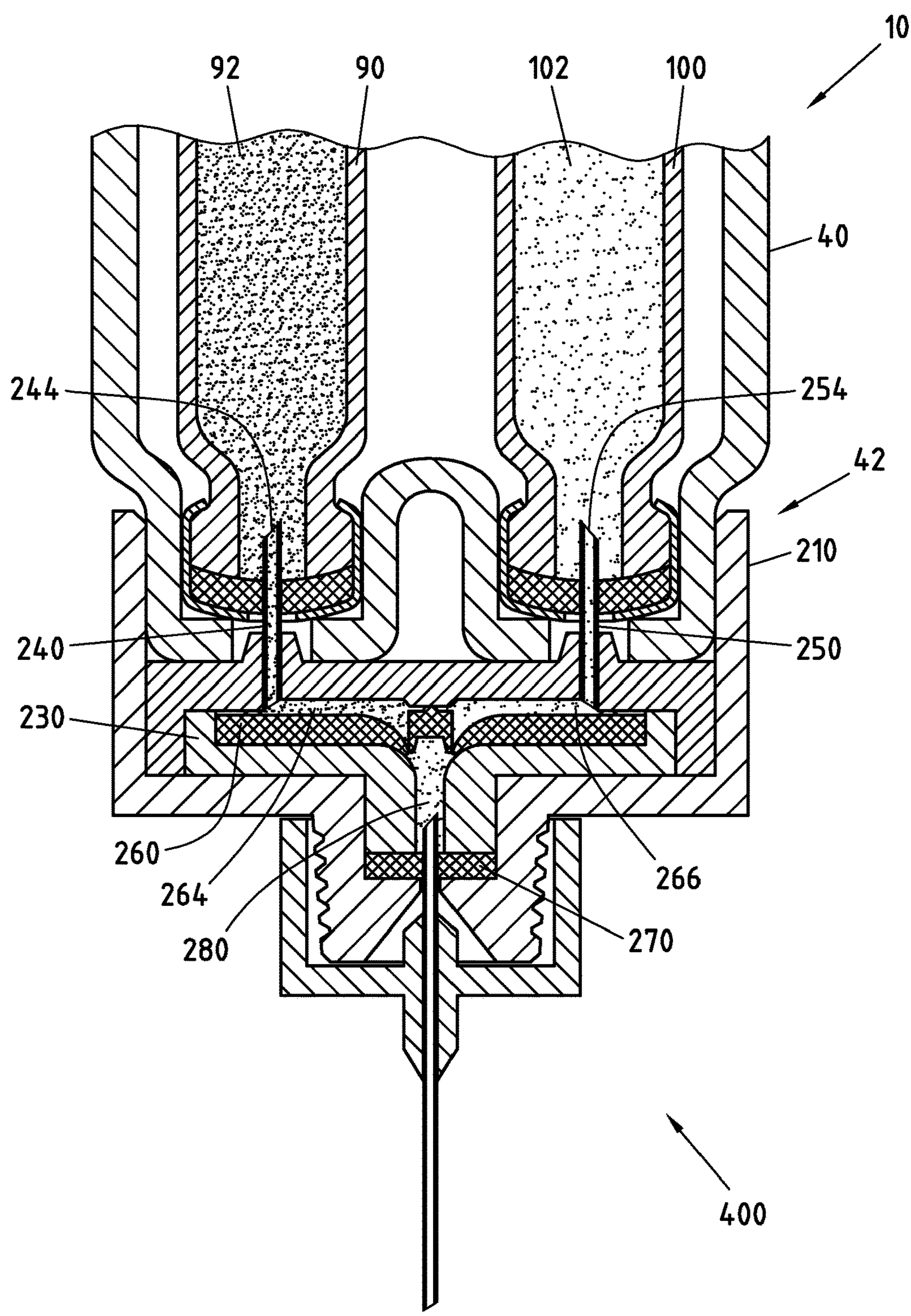
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

The electro-mechanical drive train within main body 14 of device 10 shown in FIG. 1 comprises a motor to provide the mechanical power for moving the drive train, for example to exert a pressure on the bung of cartridge 90 or 100 to eject a medicament volume out of one of these cartridges. The volume of the medicament ejected from the device directly depends on the drive train movement and thus on the motor movement. The motor movement and in particular the motor torque therefore have to be precisely controlled to achieve ejection of a precise medicament dose.

To this end, the motor of device 10 is preferably a motor that allows to be precisely controlled, such as a DC stepper motor.

Figure 12:
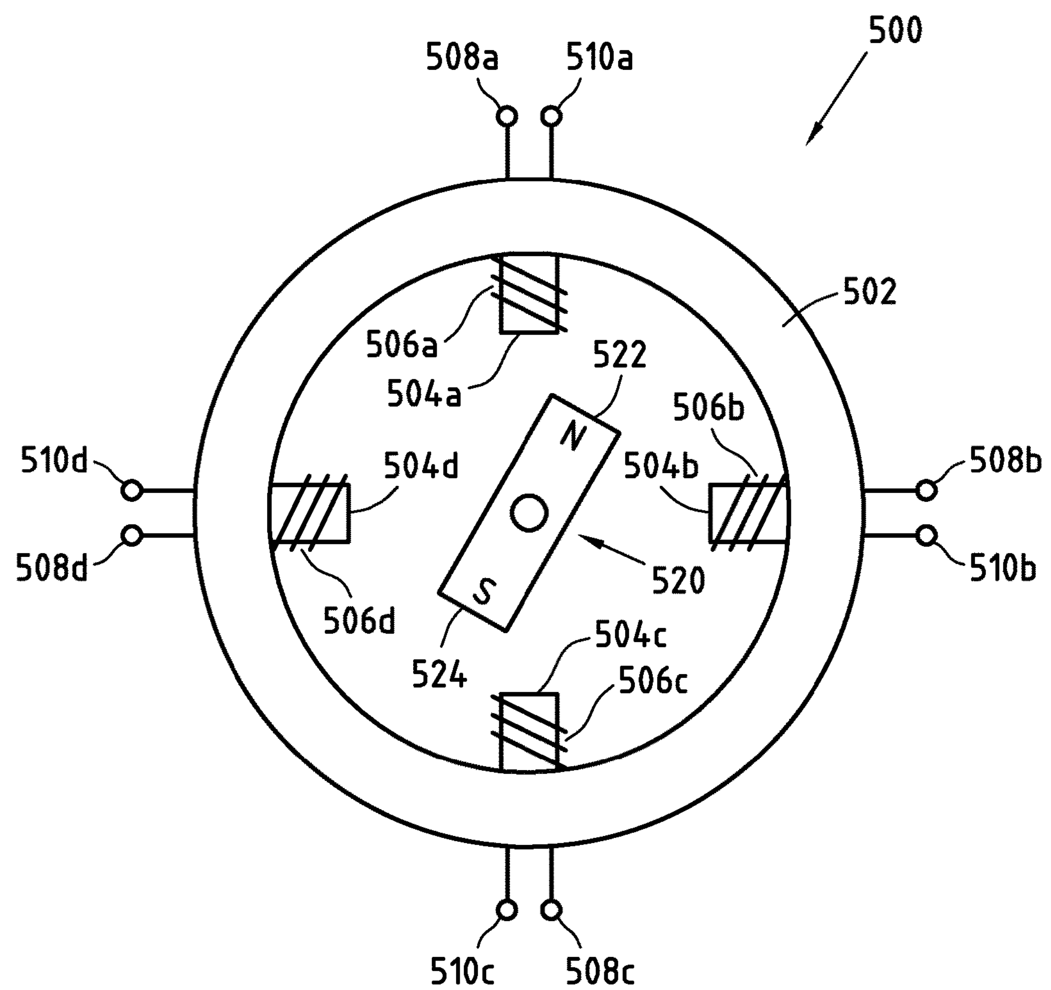
FIG. 12 shows a schematic illustration of a DC stepper motor as an example for a motor to be used for the device shown in FIG. 1.
Figure 13:
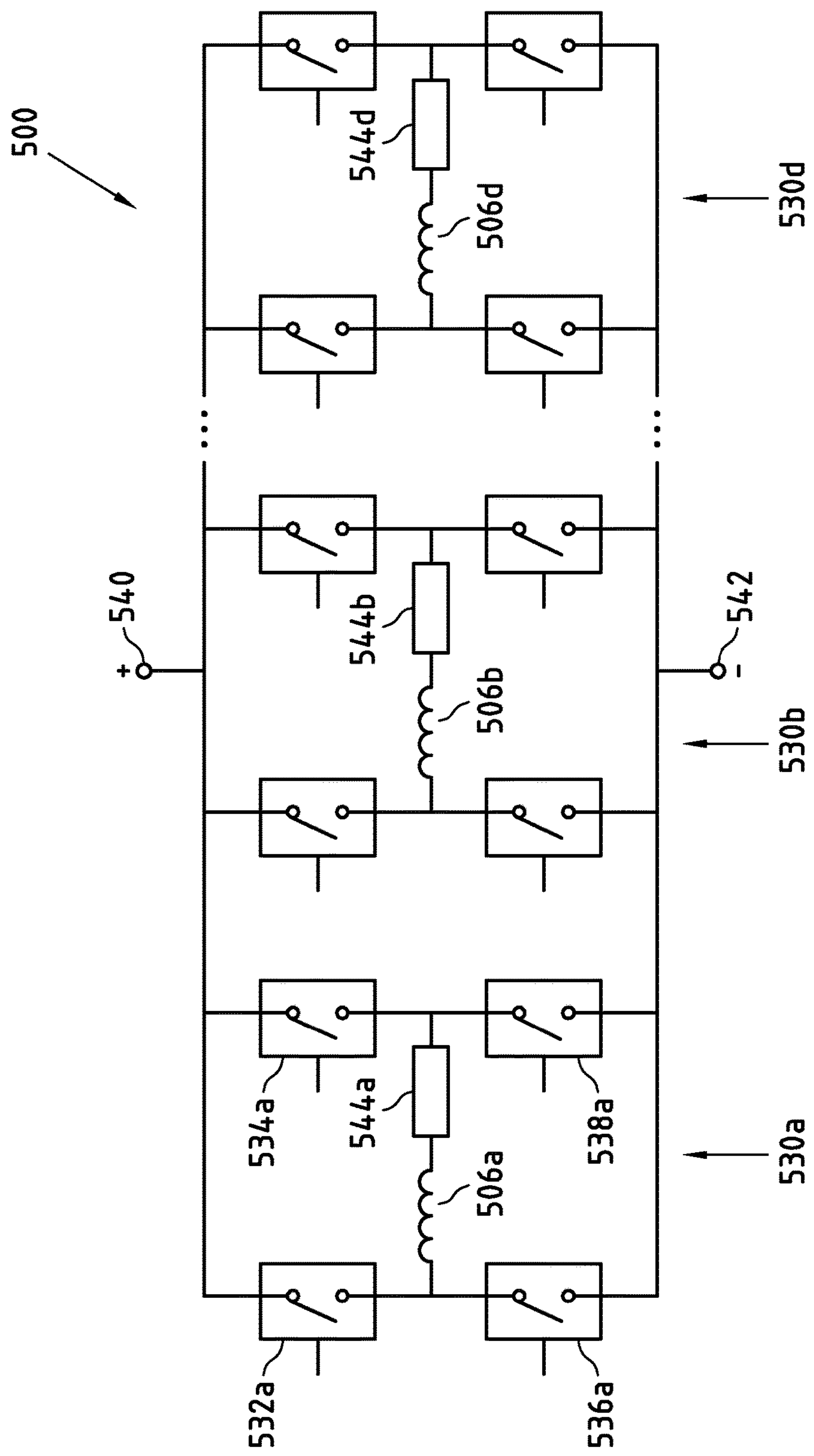
FIG. 13 shows a schematic circuit diagram of a drive circuitry of the motor shown in FIG. 12.

FIG. 12 shows a schematic illustration of such a DC stepper motor 500 that may be used for the drive train of the device 10 shown in FIG. 1. FIG. 13 shows a schematic circuit diagram of a drive circuitry of DC stepper motor 500 by means of which the motor is controlled and supplied with electrical power from a voltage source.

DC stepper motor 500 comprises a stator 502 with four poles 504*a-d*, each pole being equipped with a motor winding 506*a-d* for generating a magnetic field. Each motor winding 506*a-d* comprises a first terminal 508*a-d* and a second terminal 510*a-d* to connect the motor windings 506*a-d* to the drive circuitry shown in FIG. 13. DC stepper motor further comprises a rotor 520 which in this example is a two-pole permanent magnet with a magnetic north pole 522 and a magnetic south pole 524. Of course, the stator and/or rotor may have different numbers of poles than shown in FIG. 12. Also rotor 520 may comprise an electromagnet with motor windings instead of a permanent magnet and/or the stator may be equipped with permanent magnets.

The drive circuitry of motor 500 comprises four identical H-bridges 530*a-d*, one H-bridge for each one of motor windings 506*a-d*. (FIG. 13 only shows three of the four H-bridges for simplicity.) The setup of the H-bridges will now be described with reference to H-bridge 530*a*.

H-bridge 530*a* comprises four electronic switches: an upper left switch 532*a*, an upper right switch 534*a*, a lower left switch 536*a* and a lower right switch 538*a*. The switches may for example comprise bipolar or field effect transistors. Upper left switch 532*a* and lower left switch 536*a* connect the first terminal 508*a* (FIG. 12) of motor winding 506*a* to a positive terminal 540 and to a negative terminal 542, which are connected to a positive and negative terminal of a voltage source, respectively. Upper right switch 534*a* and lower right switch 538*a* accordingly connect the second terminal 510*a* (FIG. 12) to the positive terminal 540 and to a negative terminal 542, respectively, wherein in FIG. 13 the second terminal 510*a* is connected in series to a resistor 544*a* to limit the current flowing through motor winding 506*a* when connected to the positive and negative terminal 540, 542. The other H-bridges 530*b-d* are configured accordingly.

Switches 532*a-d*, 534*a-d*, 536*a-d* and 538*a-d* are controlled by the control unit of device 10. For example, control unit may close switches 532*a* and 538*a* and open switches 534*a* and 536*a* to apply a certain voltage to motor winding 506*a*. Motor winding 506*a* then generates a magnetic field, so that pole 504*a* constitutes for example a magnetic north pole. If the control unit instead closes switches 534*a* and 536*a* and opens switches 532*a* and 538*a* the reverse voltage is applied to motor winding 506*a*, so that pole 504*a* is for example turned into a magnetic south pole.

By alternately reversing the voltages supplied to motor windings 506*a-d* depending on the position of rotor 520, the control unit may cause the rotor 520 to rotate in a stepwise manner and therewith precisely control the motor movement.

Furthermore, the control unit is configured to control the motor torque of motor 500 by means of pulse width modulation (PWM). To this end, instead of continuously closing certain switches of H-bridges 530*a-d* for applying corresponding voltages to motor windings 506*a-d*, the control unit opens and closes the respective switches with a high frequency. The relation of the time periods during which the respective switches are closed ($T_{on}$) and during which the respective switches are open ($T_{off}$) defines the PWM duty cycle. The higher the PWM duty cycle, the higher is the mean voltage applied to motor windings 506*a-d* and thus the motor torque generated by motor 500.

During operation of device 10 there may be different movements of the drive train requiring different motor torques to be provided by motor 500. For example, when a medicament volume is to be ejected from the device, the drive train is controlled to exert a pressure on the bung of one of the two cartridges 90, 100. Depending on the viscosity of the medicament within the respective cartridge, the geometry of the device and the friction of the system this particular movement may need a certain motor torque to be provided by motor 500. The control unit may then set the PWM duty cycle to a certain value in order to achieve the required motor torque.

The motor torque achieved with a particular PWM duty cycle may however depend on the temperature of the device, in particular of the motor windings. For example, the electrical resistance of motor winding 506*a* may increase for increasing temperature, so that a smaller current flows through motor winding 506*a* when connected to a constant voltage supply. Therefore, the motor torque achieved with a particular PWM duty cycle may be smaller for a higher temperature. A temperature change may also have other effects on the device, such as a viscosity decrease of the medicament in cartridges 90, 100 or a friction decrease due to higher lubricant effectiveness and the like. Therefore, the motor torque needed for a particular movement may also depend on the temperature.

If the control unit controlled the motor 500 regardless of any temperature effect, the motor torque provided by motor 500 would not be optimal if the temperature deviates from, for example, room temperature. A loss of operational precision such as a less precise medicament ejection would be the consequence.

In order to account for such temperature-related effects and to improve operational precision for different environmental temperatures, device 10 comprises an electronic detection circuitry to determine an electrical quantity being a function of the electrical resistance of one of the motor windings 506*a-d* and the control unit is configured to control the motor 500 as a function of this electrical quantity.

Figure 14:
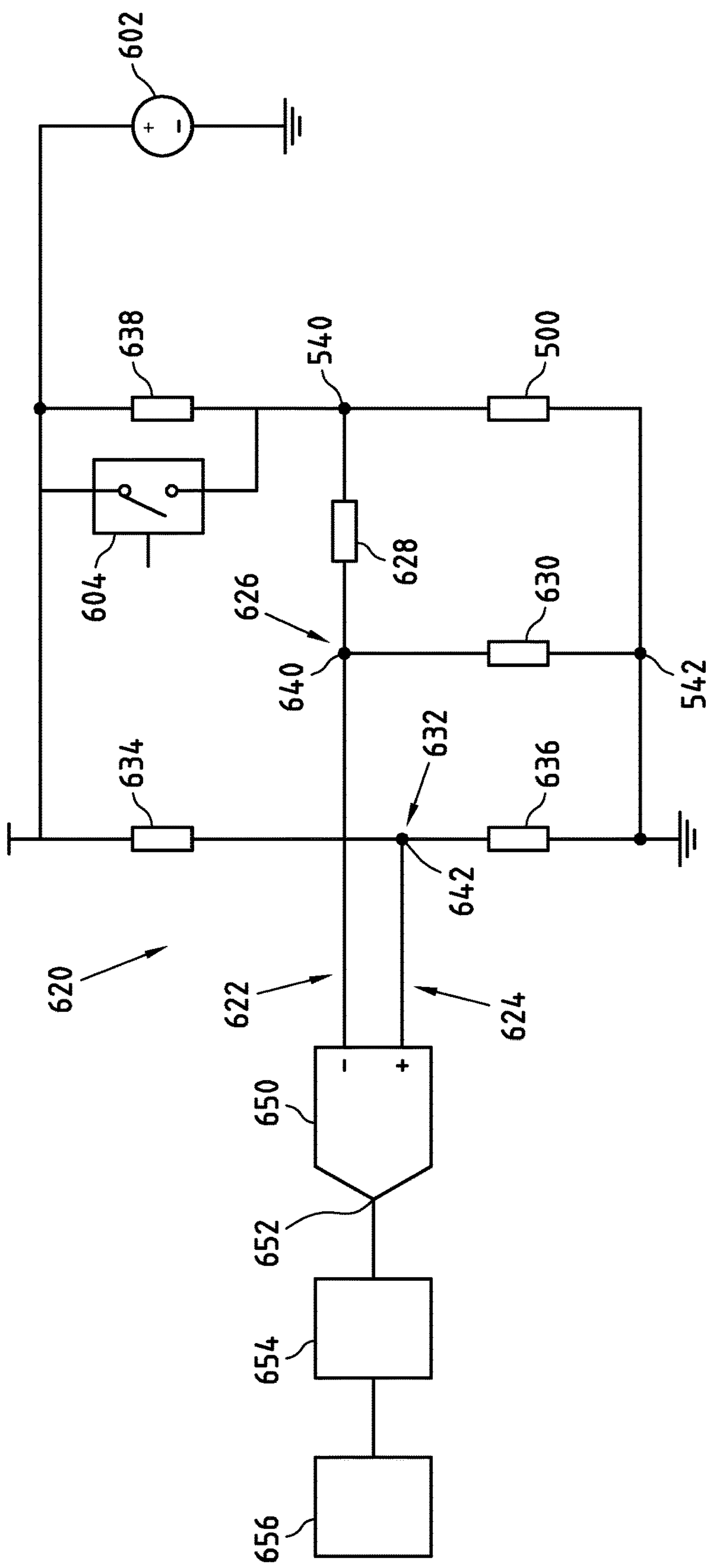
FIG. 14 shows a schematic circuit diagram with an exemplary embodiment of the electronic detection circuitry configured to determine an electrical quantity being a function of the electric resistance of one of the motor windings of the motor shown in FIG. 12.

An example for such an electronic detection circuitry will now be described with reference to FIG. 14. FIG. 14 shows a schematic circuit diagram with an exemplary embodiment of the electronic detection circuitry configured to determine an electrical quantity being a function of the electric resistance of one of the motor windings 506*a-d* of motor 500 shown in FIG. 12.

In FIG. 14, motor 500 is connected to a constant voltage source 602, more precisely positive terminal 540 of motor 500 (FIG. 13) is connected to the positive terminal of voltage source 602 over electronic switch 604 and negative terminal 542 of motor 500 (FIG. 13) is connected to the negative terminal of voltage source 602, which in FIG. 14 is connected to ground. For operating motor 500, control unit closes switch 604 and then controls the switches of H-bridges 530*a-d* as described before to cause rotor 520 to rotate.

The circuitry shown in FIG. 14 further comprises an electronic detection circuitry 620 with a first sub-circuitry 622 and a second sub-circuitry 624. The first sub-circuitry 622 comprises a first voltage divider 626 having a series connection of two resistors 628, 630 connected in parallel to motor 500, more precisely to the positive and negative terminals 540, 542 of motor 500. The second sub-circuitry 624 comprises a second voltage divider 632 with a series connection of two electrical resistors 634, 636 connected in parallel to voltage source 602. The voltage at central tap 640 of first voltage divider 626 is referred to as $U_m$ and the voltage at central tap 642 of second voltage divider 632 is referred to as $U_{ref}$.

The central taps 640, 642 of the first and second voltage divider 626, 632 are each connected to a respective input terminal of a differential amplifier 650, so that differential amplifier 650 provides at its output terminal 652 a signal being proportional to the voltage difference between central taps 640, 642 ($U_{ref}-U_m$). The analogue signal from output terminal 652 is converted to a digital signal by analogue digital converter 654 and then fed to control unit 656 which may be for example a micro-controller connect to a storage. The analogue digital converter 654 may for example be an 8-bit converter having a discrete number range of 256 discrete numbers from 0 to 255 and configured such that a zero input signal (0 V) is converted to the middle number 127.

For operation of the electronic detection circuitry 620 the motor 500 is preferably at rest and the control unit controls the switches of H-bridges 530*a*-*d* such that only one of motor windings 506*a*-*d* is connected to the positive and negative terminal 540, 542. For example, control unit may close switches 532*a* and 538*a* and open all other switches so that only motor winding 530*a* is connected to terminals 540, 542. Motor 500 may then be regarded as a simple resistor (as illustrated by the electronic symbol for motor 500 in FIG. 14) with resistance $R_m=R_w+R_r+R_{fet}$ being the sum of the series connection of the respective resistances of the motor winding 506*a* ($R_w$), of serial resistor 544*a* ($R_r$) and of switches 532*a* and 538*a* ($R_{fet}$) which may be field effect transistors for example.

Furthermore, control unit opens switch 604, so that a resistor 638 connected in parallel to switch 604 limits the current flowing through motor winding 506*a* and allows the voltage at the positive terminal 540 of motor 500 to change as a function of the resistance of motor winding 506*a*.

As voltage divider 626 is connected in parallel to motor 500, which as described before may be regarded as a resistor of resistance $R_m$, the voltage $U_m$ at central tap 640 is a function of the voltage drop over motor 500, in particular over motor winding 506*a*. Voltage divider 632 is connected in parallel to voltage source 602 and provides a reference voltage $U_{ref}$ at central tap 642 for the voltage $U_m$ at central tap 640 of first voltage divider 626. The resistances of resistors 628, 630, 634 and 636 may be selected such that the voltages $U_m$, $U_{ref}$ at central taps 640, 642 agree for a temperature of, for example, 20° C. Since $U_{ref}-U_m=0$ in this case, difference amplifier 650 will then output a signal of 0 V and thus analogue digital converter 654 will feed the middle value "127 " to control unit 656.

If due to a change in temperature the ratio between $R_m$ and the resistance of resistor 638 changes, the voltage drop over motor 500 and thus the voltage $U_m$ at central tap 640 will change as well. For example, if $R_w$ and therefore $R_m$ rises due to higher environmental temperature, $U_m$ will rise as well and differential amplifier 650 will output a negative voltage since $U_{ref}-U_m<0$ V. Analogue digital converter 654 may then accordingly output a value <127. If instead $R_w$ and therefore $R_m$ falls due to lower environmental temperature, $U_m$ will fall as well and differential amplifier 650 will output a positive voltage since $U_{ref}-U_m>0$ V. Analogue digital converter 654 may then accordingly output a value >127.

The analogue signal, i.e. the output voltage from the differential amplifier 650, or the digital signal, i.e. the digital output signal from the analogue digital converter 654, therefore respectively constitute an electrical quantity which is a function of the electric resistance of the motor winding $R_w$.

The control unit of device 10 shown in FIG. 1 is configured to control the motor 500 as a function of the output signal from the differential amplifier 650. Control unit 656 is configured to control PWM duty cycle and therewith the motor torque of motor 500 as a function of the digital signal received from analogue digital converter 654. To this end, control unit 656 comprises a storage containing a look-up table, which for each possible output value (0-255) of the analogue digital converter 654 contains a value for the PWM duty cycle. The control unit may thus select a PWM duty cycle value from the look-up table as a function of the signal from the analogue digital converter 654 and control the switches of H-bridges 530*a*-*d* of motor 500 accordingly.

Alternatively, control unit 656 may also determine the PWM duty cycle value from the signal of the analogue digital converter 654 by means of a function implemented in the computer program run by control unit 656. An example of such a function is described in the following:

The PWM duty cycle may for example be expressed as a linear function of the motor winding resistance $R_w$:

$$[PWM \text{ duty cycle } (\%)]=m \cdot R_m(\Omega)+c, \tag{1}$$

wherein m and c are parameters that may determined empirically for different types of possible motor movements of motor 500 during the operation of device 10.

Table 1 gives examples of parameters that were empirically determined for different types of motor movements of a device as shown in FIG. 1:

TABLE 1

Parameters for determining the PWM duty cycle for different types of motor movements

| Type of motor movement | m | c |
|---|---|---|
| Dispense at 6 u/s | 5.207 | 7.448 |
| Dispense at 9 u/s | 5.658 | 3.809 |
| Drive train retraction | 5.207 | 0.948 |

During medicament dispense, the drive train has to exert a pressure on a bung of at least one cartridge 90, 100 and thus the motor 500 has to provide a certain motor torque to overcome the resistance of the bung due to friction or medicament viscosity. For a lower dispense rate of for example 6 volume units per second (u/s) a lower motor torque is required than for a higher dispense rate of 9 u/s. For retraction of the drive train to its home position, even less motor torque is needed. Table 1 therefore contains different parameters m and c for all of these different types of motor movement.

The storage connected to control unit 656 may for example contain a table like table 1 with values for m and c for different types of motor movements. Of course the storage may comprise values for m and c for more and/or different types of motor movements as described in table 1.

Depending on the type of motor movement to be performed next by motor 500, control unit 656 may then fetch from the storage the according values for m and c, determine $R_m$ from the signal from the analogue digital converter 654 and calculate the adequate PWM duty cycle by means of equation (1). The PWM duty cycle according to equation (1) may of course also be expressed as a function of the signal from the analogue digital converter 654 so that control unit 656 may directly determine the PWM duty cycle from the signal received from the analogue digital converter 654.

Since $R_m$ is a function of the temperature of the motor winding 506*a* and since the parameters for controlling motor 500, such as the PWM duty cycle, are controlled as a function of $R_m$, temperature-related effects on the motor torque provided by motor 500 or required for different types of motor movements can be accounted for. In particular, the $R_m$-dependence and thus temperature-dependence of equation (1) is configured such, that temperature-related effects are counteracted and thus the motor torque required for a certain temperature is precisely provided by means of the control unit controlling the motor 500 as a function of $R_m$. Device 10 therefore provides high motor movement precision and thus high medicament ejection precision for different operating temperatures.

An example for an actual configuration of the electronic detection circuitry 620 and an according example of calculation will be described in the following:

Voltage source 602 may be configured to provide a voltage $U_s$ of 5.5 V and the resistance values of the electronic detection circuitry 620 and of resistance 638 shown in FIG. 14 may be selected as summarized in table 2:

TABLE 2

Exemplary resistance values for the circuitry in FIG. 14

| Resistor | Resistance value |
|---|---|
| first voltage divider: resistor 628 | 22 kΩ |
| first voltage divider: resistor 630 | 11 kΩ |
| second voltage divider: resistor 634 | 15 kΩ |
| second voltage divider: resistor 636 | 3 kΩ |
| resistor 638 | 16 Ω |

Typical temperature dependences of the resistance $R_w$ of motor winding 506*a*, of the resistance $R_r$ of serial resistor 544*a* and of the resistance $R_{fet}$ of switches 532*a* and 538*a* may be as follows:

$$R_w = 14\Omega\cdot(1+\alpha_w\cdot(T-20^\circ\ \mathrm{C.})),$$

where $\alpha_w = 3.9\cdot\Omega 10^{-3}\Omega/^\circ$ C. for a copper winding;

$$R_r = 1.5\Omega\cdot(1+\alpha r\cdot(T-20^\circ\ \mathrm{C.})),$$

where $\alpha_r = 0.2\cdot 10^{-3}\Omega/^\circ$ C.; and $$R_{fet} = 0.8\Omega\cdot(1+\alpha_{fet}\cdot(T-20^\circ\ \mathrm{C.})),$$

where $\alpha_{fet} = 4.0\cdot 10^{-3}\Omega/^\circ$ C.;

wherein T is the temperature in ° C. and the motor resistance $R_m$ is given by $R_m = R_w + R_r + R_{fet}$. Of course, resistor 638 or other electronic components in the circuitry may have a temperature-dependence as well, which may be accounted for by the control unit. In the present example these temperature-dependencies are assumed to be negligible for the sake of clarity.

With the resistance values of the resistors 634, 636 of the second voltage divider, the voltage $U_{ref}$ at the positive input terminal of differential amplifier 650 is given by (resistance of resistor 636 is denoted as $R_{636}$ etc.):

$$U_{ref} = U_s\cdot R_{636}/(R_{634}+R_{636}) = U_s\cdot 3\ \mathrm{k\Omega}/(15\ \mathrm{k\Omega}+3\ \mathrm{k\Omega}) = U_s/6 = 5.5\ \mathrm{V}/6 \approx 0.92\ \mathrm{V}.$$

At a temperature of 15° C. with $R_m \approx 16\Omega$, $U_m$ is given by:

$$U_m = U_s\cdot R_m/(R_{638}+R_m)\cdot R_{630}/(R_{628}+R_{630}) = U_s\cdot R_m/(R_{638}+R_m)\cdot 1/3 \approx 0.92\ \mathrm{V},$$

so that $U_{ref}-U_m \approx 0$ V. In this example, the electronic detection circuit is therefore configured such that the difference $U_{ref}-U_m \approx 0$ V and thus also the output signal of differential amplifier 650 is about 0 V for a temperature of about 15° C.

A typical temperature range for operation of the device 10 is between 2° C. and 60° C. The minimum expected value of $R_m$ at 2° C. is therefore 15.3Ω, so that $U_m \approx 0.90$ V, and the maximum expected value of $R_m$ at 60° C. is 18.6Ω, so that $U_m \approx 0.99$ V. In the temperature range between 2° C. and 60° C., the difference $U_{ref}-U_m$ therefore varies between +20 mV and −70 mV.

The output signal $U_{amp}$ of differential amplifier 650 may be expressed by $U_{amp} = a\cdot(U_{ref}-U_m)$, wherein a is the gain factor of differential amplifier 650. Differential amplifier may be a programmable differential amplifier (PGA) which may be programmed to have a gain factor a in the range from 1 to 32. In electronic detection circuitry 620, a is preferably selected such that the voltage range output by differential amplifier 650 is adapted to the input range of analogue digital converter 654. For the exemplary layout of electronic detection circuit 620 described above, a may for example be 20, so that in the temperature range between 2° C. and 60° C. the differential amplifier 650 outputs voltages in the range between +0.4 V and −1.4 V.

The analogue digital converter 656 may be configured such that an input voltage in the range between +0.4 V and −1.4 V is converted to the full number range of from 0 to 255 so that the maximum resolution of analogue digital conversion is achieved without clipping. The digital signal value output by analogue digital converter 656 is an electrical quantity which is a function of the resistance of motor winding 506*a* and therefore also of the temperature of motor winding 506*a*. With control unit 656 controlling the PWM duty cycle as a function of the value output by the analogue digital converter 656, the PWM duty cycle is selected such that motor 500 provides the adequate motor torque for each temperature within the temperature range between 2° C. and 60° C.

With the exemplary embodiment described before it is therefore possible to control the movement of the drive train for different motor scenarios with very high precision even at different temperatures of the motor winding. Therefore, device 10 provides a high dosage precision for a broad range of temperatures, so that for example the dosage is as precise during summer when temperatures are high as it is during winter when temperatures are low.

During motor operation, resistor 638 is short-circuited by switch 604 so that the voltage drop over motor 500 is 5.5 V, which is the voltage provided by the voltage source 602. The ratio of the resistances of resistors 628 and 630 of the first voltage divider 626 is selected such that the voltage applied to the differential amplifier 650 and then to the digital analogue converter 654 stays within a safe range. Electrical detection circuit 620 therefore does not affect motor operation or vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus for ejecting a fluid, the apparatus comprising:

an electric motor comprising at least one motor winding;

a control unit for controlling the motor; and an electronic detection circuitry configured to determine an electrical quantity, the electrical quantity being a function of the electric resistance ($R_w$) of the motor winding, wherein the control unit is configured to control the motor as a function of the electrical quantity, wherein the electronic detection circuitry comprises an analogue digital converter configured to convert the electrical quantity from an analogue signal to a digital signal, wherein the analogue digital converter has a discrete number range of possible outputs and wherein the analogue digital converter is configured such that a middle number of the number range is output for an analogue signal of the electrical quantity for a motor winding temperature between 10° C. and 40° C.

2. The apparatus according to claim 1, wherein the electric motor is a DC motor, and wherein the apparatus comprises a DC voltage source configured to supply a voltage to the at least one motor winding.

3. The apparatus according to claim 2, wherein the DC motor is a DC stepper motor.

4. The apparatus according to claim 1, wherein the electrical quantity is a voltage.

5. The apparatus according to claim 1, wherein the detection circuitry comprises:

a first sub-circuitry configured to provide a first voltage being a function of a first voltage drop over the motor winding; and a second sub-circuitry configured to provide a second voltage being a function of a voltage source, the voltage source being configured to supply voltage to the motor winding, wherein the electrical quantity is a function of the difference between the first and the second voltage.

6. The apparatus according to claim 5, wherein the detection circuitry comprises a differential amplifier having two input terminals and an output terminal, wherein the first sub-circuitry comprises a first voltage divider connected in parallel to the motor winding, a central tap of the first voltage divider being connected to a first of the two input terminals of the differential amplifier, and wherein the second sub-circuitry comprises a second voltage divider connected in parallel to the voltage source, a central tap of the second voltage divider connected to a second of the two input terminals of the differential amplifier.

7. The apparatus according to claim 1, further comprising:

a pulse width modulation (PWM) circuitry configured to control the motor torque by pulse width modulation, wherein the control unit is configured to control the PWM duty cycle as a function of the electrical quantity.

8. The apparatus according to claim 1, wherein the control unit is configured to estimate the temperature of the at least one motor winding as a function of the electrical quantity.

9. The apparatus according to claim 1, wherein the control unit is configured to control the electronic detection circuitry to determine the electrical quantity when the motor is at rest.

10. The apparatus according to claim 1, wherein the apparatus is a medical device.

11. The apparatus according to claim 10, wherein the medical device is a medicament injection device.

12. The apparatus according to claim 1, wherein the apparatus is hand-held.

13. A method for controlling an apparatus, wherein the apparatus comprises:

an electric motor comprising at least one motor winding;

a control unit for controlling the motor; and an electronic detection circuitry comprising an analogue digital converter configured to convert the electrical quantity from an analogue signal to a digital signal, wherein the analogue digital converter has a discrete number range of possible outputs and wherein the analogue digital converter is configured such that a middle number of the number range is output for an analogue signal of the electrical quantity for a motor winding temperature between 10° C. and 40° C., wherein the method comprises:

determining an electrical quantity, the electrical quantity being a function of the electric resistance ($R_w$) of the motor winding, the electrical quantity received as an analogue signal;

converting the analogue signal into a digital signal; and controlling the motor as a function of the digital signal.

14. The method according to claim 13, wherein the electrical quantity is determined when the motor is at rest.

* * * * *